United States Patent [19]

Fideler

[11] Patent Number: 5,327,906
[45] Date of Patent: Jul. 12, 1994

[54] STEERABLE STYLET HANDLE

[75] Inventor: Brian L. Fideler, Columbia Heights, Minn.

[73] Assignee: Medtronic, Inc., Minneapolis, Minn.

[21] Appl. No.: 55,947

[22] Filed: Apr. 28, 1993

[51] Int. Cl.$^5$ ............................................. A61B 5/00
[52] U.S. Cl. ................................... 128/772; 604/95
[58] Field of Search ...................... 128/657, 772, 658; 604/95, 280; 606/46, 47

[56] References Cited

U.S. PATENT DOCUMENTS

| | | |
|---|---|---|
| 3,416,531 | 12/1968 | Edwards . |
| 3,452,740 | 7/1969 | Muller . |
| 3,503,385 | 3/1970 | Stevens . |
| 3,647,103 | 12/1970 | Cook . |
| 4,215,703 | 8/1980 | Willson ................ 128/772 |
| 4,650,467 | 3/1987 | Bonello ................ 604/95 |
| 4,732,163 | 3/1988 | Bonello ................ 128/772 |
| 4,757,827 | 7/1988 | Buchbinder ......... 128/772 |
| 5,199,950 | 4/1993 | Schmitt et al. ....... 604/95 |

FOREIGN PATENT DOCUMENTS 9111213  8/1991  World Int. Prop. O. ............ 604/95

*Primary Examiner*—Max Hindenburg
*Attorney, Agent, or Firm*—Reed A. Duthler; Harold R. Patton

[57] ABSTRACT

A control handle for a steerable stylet or guidewire which is specifically adapted to facilitate one-hand operation by providing a rear gripping portion adapted to be held in the palm of the operator's hand and gripped by the last three fingers, and having a rotatable control sleeve for actuation by the thumb and forefinger of the operator's hand, the control sleeve having internal actuating threads meshing with the threads of a slide which is fixed to the proximal end of a stylet control wire for permitting adjustment of the curvature of the distal tip portion of the stylet. The stylet, control wire and slide are removable from the rest of the handle assembly, to allow for replacement or interchange of stylets.

7 Claims, 2 Drawing Sheets

STEERABLE STYLET HANDLE

BACKGROUND OF THE INVENTION

The present invention relates generally to medical lead and catheters and more particularly to a deflectable stylet assembly for use therewith.

A number of different devices have been provided for performing the controlled deflection of the curved distal portion of a stylet or guidewire. Such devices are disclosed in the following U.S. Patents: Buchbinder, et al., U.S. Pat. No. 4,757,827; Bonello and Jeanmonod, U.S. Pat. No. 4,650,467; Bonello and Jeanmonod, No. 4,732,163; Willson, U.S. Pat. No. 4,215,703; Stevens, U.S. Pat. No. 3,503,385; Cook, U.S. Pat. No. 3,547,103; Muller, U.S. Pat. No. 3,452,740; and, Edwards, No. 3,416,531. While these devices have worked reasonably well, many of the prior art devices require the use of both hands of the operator, and the control mechanism in each of the prior art units is permanently attached to the proximal end of the stylet or guidewire and cannot be readily detached for use with another stylet or guidewire. Also, the prior art devices are all limited to a fixed degree of deflection for a given movement of the deflection control element.

SUMMARY OF THE INVENTION

It is a principal object of the present invention to provide a versatile handle assembly for a steerable stylet or guidewire, particularly designed to permit one-hand operation for imparting controlled deflection to the distal tip thereof. The disclosed embodiment of the invention takes the form of a deflectable stylet particularly adapted for use in conjunction with implantable electrode leads such as cardiac pacing leads.

One-hand operation of the stylet is facilitated by providing a gripping handle at the proximal end of the handle assembly, adapted to be securely held in the palm of the operator's hand and having a control element located adjacent the distal end of the control handle assembly, for actuation by the thumb and/or forefinger of the operator's hand. The control element is connected with a slide member attached to the proximal end of a control wire which is longitudinally displaced to cause curvature of the steerable tip portion of the stylet.

A substantial portion of the control handle assembly can be removed from the stylet and is interchangeable with the other stylets. This permits the handle to be sterilized separately from the lead or catheter so that the same handle assembly can be used to control different stylets. This not only reduces the cost of the control units, but also facilitates easy interchange of stylet assemblies to provide varied deflection characteristics.

DETAILED DESCRIPTION OF THE DRAWINGS

DETAILED DESCRIPTION OF THE INVENTION

Figure 1:
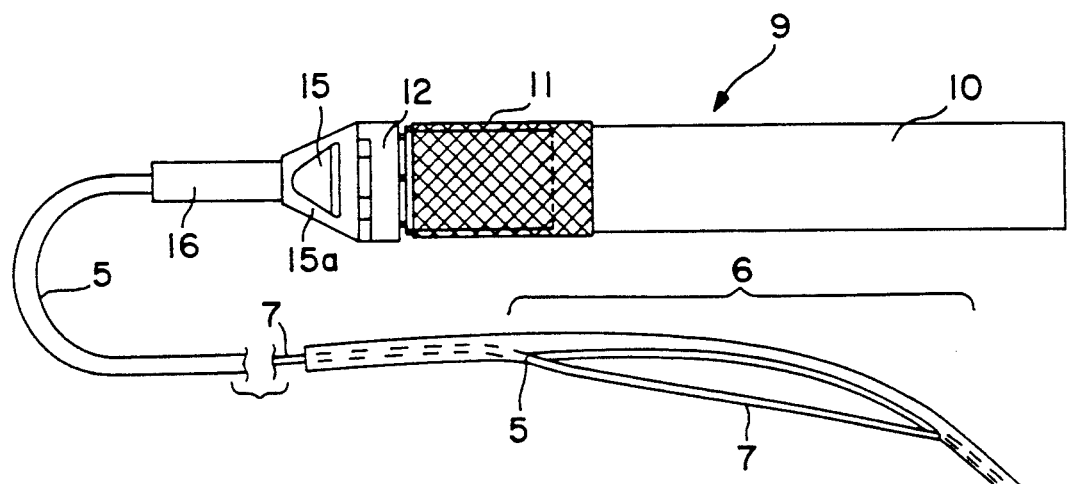
FIG. 1 is a side elevation of a handle and stylet assembly embodying the invention.

A steerable stylet is illustrated in FIG. 1 for use with an intravenous pacing lead. The curvature of the stylet 5, and thus of the electrode lead in which it is located in use, can be dynamically and continuously controlled by retraction and projection of a control wire 7, slidably mounted within the tubular body of stylet 5 to provide bending control for the distal tip 6 of the stylet 5. Retraction of the control wire 7 produces increased curvature in the tip 6, as illustrated.

The control handle assembly 9 includes a grip 10 at its proximal end, a control sleeve 11 rotatably mounted distal to the grip 10. The grip portion 10 i held in the palm of the operator's hand as by the last three fingers of the hand. The rotatable control sleeve 11 is rotated by the thumb and forefinger of the operator's hand, causing projection or retraction of control wire 7 to straighten or deflect the stylet 5. The mounting position of control sleeve 11 results in easy and sensitive one-hand control. Control sleeve 11 is mounted around an internal mounting body 12, the distal end of which is visible in FIG. 1. The stylet 5 is mounted to a removable nose-cone 15, provided with two opposing flattened surfaces 15a. A stress relief sleeve 16 is provided at the junction of the stylet 5 and the nose cone 15.

Figure 2:
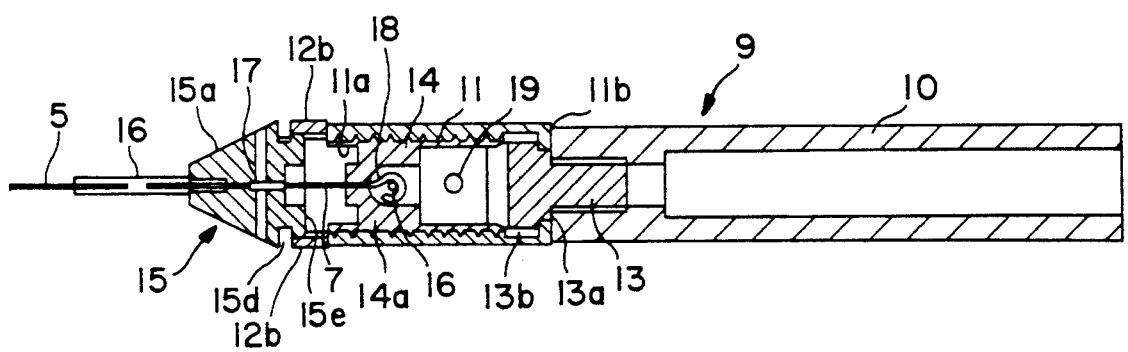
FIG. 2 is a longitudinal section, showing the handle assembly with a portion of a stylet attached thereto.

FIG. 2 illustrates the control handle assembly in cross section. The sleeve 11 is provided with internal threads 11a and a circumferential collar 11b which rotates in a retaining groove formed between the distal end of the grip 10 and the proximal end portion of an internal mounting body 12, (illustrated in detail in FIG. 3). The mounting body 12 is attached to the grip 10 by an externally threaded spindle 13 which is received in the internally threaded distal end of the grip 10. The distal end of the grip 10 abuts a circumferential shoulder 13a which provides a stop for the distal end of the grip 10. The collar 11b of the control sleeve 11 rotates in the circumferential groove formed between the distal end of the grip 10 and a second shoulder 13b on the mounting body 12.

The internal mounting body 12 has a central guiding slot in which an actuating slide 14, is slidably mounted. The slide 14 is provided with generally flat sidewalls 14a and threaded edges, which mesh with the internal threads of the control sleeve 11. When the control sleeve 11 is rotated, the slide 14 is correspondingly moved in the guiding slot within the mounting body 12. Sleeve 16 surrounds the handle end of the stylet and is fixed to the nose cone 15. The proximal end of the stylet 5 is securely anchored to the tip as by a crimp sleeve 17. The proximal end of wire 7 is securely anchored to the actuating slide 14 as by a sleeve 18, which is a length of tubing glued around the proximal end of control wire 7, bent into a loop and retained to slide 14 by pin or screw 16.

A stop pin 19 extends across the guiding slot in mounting body 12, which limits the rearward travel of the slide 14. The maximum travel of the slide 14 controls the maximum degree of curvature obtainable in the bendable tip portion of the stylet 5. The available range of curvature can thus be readily varied by merely changing the length of the slide 14.

The amount of movement of the control wire 7 relative to the stylet 5, for a given amount of rotation of the control sleeve 11 can be changed by providing an actuating slide 14 having a different pitch on the threaded edge portions 14b and also changing the pitch of the threads of the actuating control sleeve 11 to match the thread pitch of the modified actuating slide 14. Modification of the pitches of the threads may be desirable, for instance, if the length of the deflectable portion 6 of the stylet 5 is varied.

Figure 3:
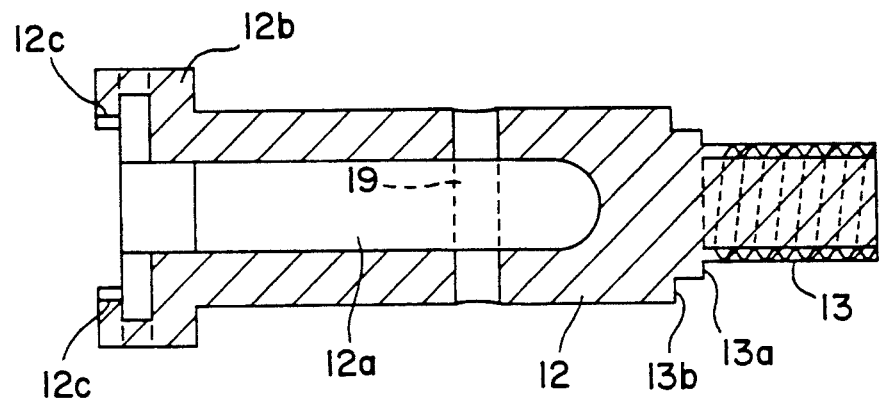
FIG. 3 is a longitudinal sectional view of the internal mounting body, within the control handle assembly.
Figure 4:
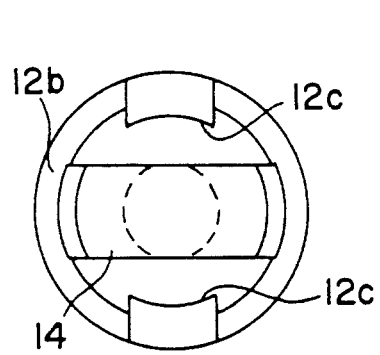
FIG. 4 is a front end view of the mounting body with an actuating slide shown in assembled position.
Figure 5:
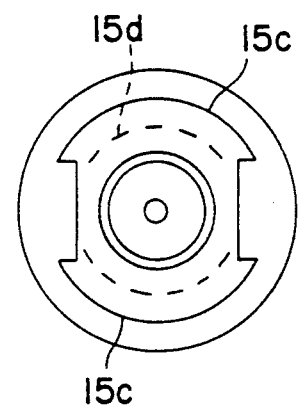
FIG. 5 is a view of the proximal end of the nose cone portion of the handle assembly.

FIG. 3 shows the mounting body in cross section. In this view the guiding slot 12a is visible. The distal end portion of the mounting body 12 has a circumferential attachment flange 12b provided with a pair of opposed, spaced-apart, inwardly directed ears 12c (illustrated in detail in FIG. 4). Nose cone 15 is connected to the distal end of the mounting body 12 as by flange segments 15c (illustrated in detail in FIG. 5), which extend from the proximal end 15d of nose-cone 15 and are retained by ears 12c. The cone can be locked into operative position by rotation through approximately 90 degrees whereby the flange segments 15c are interlocked with the ears 12c, as shown in FIGS. 4 and 5.

Exchange of stylets is accomplished by rotating nose cone 15 such that the flanges 15c are no longer engaged with ears 12c, and rotating control sleeve 11 to move the slide 14 distally until the threads of the slide 14 no longer engage the threads of the control sleeve 11. The stylet 5, nose cone 15, control wire 7 and slide 14 are then removed as a unit. Alternatively, the loop formed by sleeve 16 may be removed from slide 14, so that slide 14 may be re-used with a new stylet assembly. A corresponding stylet assembly may be installed by reversing these steps. For example, a stylet assembly having a shorter or longer deflectable portion 6 (FIG. 1) may be or a shorter or longer slide may be substituted to vary the deflection characteristics.

In the event that a change in the relative amount of movement of the control wire for a given amount of rotation of the control sleeve is desired, the mounting body 12 may be unscrewed from the grip 10 so that control sleeve 11 may also be replaced, whereby alteration of the pitch of the threads of the control sleeve and slide may be accomplished.

While the embodiment disclosed above takes the form of a deflectable stylet for use with an electrode lead, the invention may also be practiced in conjunction with a deflectable guide wire, for use in locating indwelling catheters. Indeed, the disclosed control handle may usefully be employed in conjunction with any catheter, guide-wire, stylet or similar apparatus having an elongated body and having an operative feature activated by means of displacement of a control wire located therein. As such, the above disclosure should be considered exemplary, rather than limiting with regard to the scope of the claims which follow.

I claim:

1. Medical apparatus for insertion into the body of a patient, said apparatus comprising:
   an elongated body and a longitudinally displaceable control wire mounted therein;
   a grip having a proximal end adapted to be held in the palm of one hand of an operator, and having a distal end,
   slide guiding means located at the distal end of the grip, a proximal end of said elongated body mounted to said guiding means;
   a control slide connected to a proximal end of said control wire and mounted for sliding movement relative to said guiding means;
   a slide actuating member connected with said slide and mounted at the distal end of said grip for actuation by the operators' hand to produce longitudinal movement of said slide relative to said guiding means whereby longitudinal movement of said control wire is produced with respect to said elongated body; and
   a tip member, fixedly mounted to said proximal end of said elongated body member and removably mounted to said guiding means; and
   wherein said slide is slidably mounted with respect to said guiding means such that after removal of said tip member from said guiding means, said slide may be withdrawn from said guiding means.

2. An apparatus according to claim 1 wherein said slide actuating member comprises a cylindrical sleeve rotatably mounted around said guiding means and having internal threads, and wherein said slide is provided with external threads meshing with said internal threads of said cylindrical sleeve.

3. A control handle for guiding a steerable stylet assembly including a flexible hollow tubular body having a proximal end and a bendable distal tip portion and having a control wire connected to said bendable tip portion and slidable within said tubular body for imparting a controlled curvature in the bendable tip portion, said handle comprising:
   a grip having a proximal end adapted to be held in the palm of one hand of an operator, and having a distal end,
   slide guiding means located at the distal end of the grip, a proximal end of said tubular body mounted to said guiding means;
   a control slide connected to a proximal end of said control wire and mounted for sliding movement on relative to said guiding means;
   a slide actuating member connected with said slide and mounted at the distal end of said grip for actuation by the operators' hand to produce longitudinal movement of said slide relative to said guiding means whereby longitudinal movement of said control wire is produced with respect to said tubular body; and
   a tip member, fixedly mounted to said proximal end of said tubular body and removably mounted to said guiding means; and
   wherein said slide is slidably mounted with respect to said guiding means such that after removal of said tip member from said guiding means, said slide may be withdrawn from said guiding means.

4. An apparatus according to claim 3 wherein said slide actuating member comprises a cylindrical sleeve rotatably mounted around said guiding means and having internal threads, and wherein said slide is provided with external threads meshing with said internal threads of said cylindrical sleeve.

5. Medical apparatus for insertion into the body of a patient, said apparatus comprising:
   an elongated body and a longitudinally displaceable control wire mounted therein;
   a grip having a proximal end adapted to be held in the palm of one hand of an operator, and having a distal end,
   a slide guide located at the distal end of the grip and having a longitudinally extending slot, a proximal end of said elongated body mounted to said slide guide;
   a control slide connected to a proximal end of said control wire and mounted in said longitudinally extending slot, mounted for non-rotational sliding movement relative to said slide guide; and a slide actuating member connected with said slide and mounted at the distal end of said grip for actuation by the operators' hand to produce longitudinal movement of said slide relative to said guiding means whereby longitudinal movement of said control wire is produced with respect to said elongated body.

6. An apparatus according to claim 5 wherein said slide actuating member comprises a cylindrical sleeve rotatably mounted around said guiding means and having internal threads, and wherein said slide is provided with external threads extending from said longitudinally extending slot and meshing with said internal threads of said cylindrical sleeve.

7. An apparatus according to claim 5 or claim 6, further comprising:

a tip member, fixedly mounted to said proximal end of said elongated body member and removably mounted to a distal end of said slide guide; and wherein said longitudinally extending slot of said slide guide is open to said distal end of said slide guide such that after removal of said tip member from said guiding means, said slide may be withdrawn from said slide guide.

* * * * *